United States Patent [19]

Leaf et al.

[11] Patent Number: 5,760,081

[45] Date of Patent: Jun. 2, 1998

[54] OMEGA 3 FATTY ACIDS IN THE PREVENTION OF VENTRICULAR FIBRILLATION

[75] Inventors: Alexander Leaf, Winchester; Haifa Hallaq, Boston, both of Mass.

[73] Assignee: The General Hospital Corporation, Boston, Mass.

[21] Appl. No.: 538,837

[22] Filed: Oct. 4, 1995

Related U.S. Application Data

[63] Continuation of Ser. No. 240,824, May 10, 1994, abandoned.

[51] Int. Cl.$^6$ .............................. A01N 37/00; A61K 31/20
[52] U.S. Cl. ........................................................ 514/560
[58] Field of Search ................................................ 514/560

[56] References Cited

U.S. PATENT DOCUMENTS 4,920,098  4/1990  Cotter et al. ................................. 514/2

FOREIGN PATENT DOCUMENTS 2-136952  1/1992  Japan .

OTHER PUBLICATIONS

Juan et al., Br. J. Pharamac. 90, pp. 315–325, 1987.

Hock et al., "Influence of dietary n–3 fatty acids on myocardial ischemia and reperfusion", American Journal of Physiology, vol. 259, No. 5, Nov. 1990.

Kamp et al., "pH gradients across phospholipid membranes caused by fast flip–flop of un–ionized fatty acids", Proc. Natl. Acad. Sci. USA, vol. 89, pp. 11367–11370, Dec. 1992, Biophysics.

Kang and Leaf, "Effects of long–chain polyunsaturated fatty acids on the contraction of neonatal rat cardiac myocytes," Proc. Natl. Acad. Sci. USA 91:9886–9890, 1994.

Xiao et al., "Blocking effects of polyunsaturated fatty acids on Na + channels of neonatal rat ventricular myocytes," Proc. Natl. Acad. Sci. USA, 1995.

Kang, Xiao and Leaf, "Free, long–chain polynsaturated fatty acids reduce membrane electrical excitability in neonatal rat cardiac myocytes," Proc. Natl. Acad. Sci. USA 92:3997–4001, 1995.

*Primary Examiner*—Marianne M. Cintins
*Assistant Examiner*—Dwayne C. Jones
*Attorney, Agent, or Firm*—Fish & Richardson P.C.

[57] ABSTRACT

Methods and compositions for the prevention of imminent ventricular fibrillation are disclosed. The composition comprises eicosapentaenoic acid (EPA), docosahexaenoic acid (DHA), or a mixture of EPA and DHA. The composition may be administered by intravenous infusion, intracardial injection or both in a patient who presents symptoms of a condition, such as myocardial infarction, which may immediately lead to ventricular fibrillation.

16 Claims, 1 Drawing Sheet

OMEGA 3 FATTY ACIDS IN THE PREVENTION OF VENTRICULAR FIBRILLATION

This is a continuation of application Ser. No. 08/240,824, filed May 10, 1994, now abandoned.

STATEMENT AS TO FEDERALLY SPONSORED RESEARCH

This invention was made with government support under grant number RO1-DK38165 and under grant number RO1-DA05917, both awarded by the National Institutes of Health. The government has certain rights to the invention.

BACKGROUND OF THE INVENTION

The invention relates to the prevention of ventricular fibrillation. Ventricular fibrillation can lead to sudden death, and occurs primarily in patients having myocardial infarction or other conditions which cause ischemia of cardiac tissue. The high incidence of recurrent ventricular fibrillation and sudden death in survivors of cardiac arrest underscores the need for an effective approach to prophylactic treatment in these patients.

SUMMARY OF THE INVENTION

In general, the invention features the intravenous administration of calcium channel blocking omega 3 fatty acids, particularly eicosapentaenoic acid (EPA) and docosahexaenoic acid (DHA), for the prevention of imminent ventricular fibrillation in susceptible patients including those who present with heart attack symptoms, are experiencing anaphylactic shock (e.g., induced by a bee sting), have a pre-existing condition such as a previous myocardial infarction, are receiving treatment by electrical stimulation or with antiarrhythmic drugs which may have adverse side effects, or present with some other condition which is associated with myocardial ischemia.

Preferably, an intravenous infusion of an emulsion of EPA, DHA or a mixture of EPA and DHA (the EPA-DHA emulsion) is administered as an emergency treatment of a patient identified as being susceptible to ventricular fibrillation, particularly a patient who presents with heart attack symptoms such as chest pain, light-headedness or dizziness, faintness, shortness of breath and electrocardiographic abnormalities. The infusion treatment may be continued until the patient is stabilized and appears to no longer be at risk of imminent ventricular fibrillation.

Alternatively, the patient requiring emergency treatment may receive treatment by direct injection of the EPA-DHA emulsion into the heart or an artery of the heart. Administration of this initial bolus of EPA-DHA may be followed by continuous intravenous infusion.

In a further embodiment, intravenous infusion of the EPA-DHA emulsion may be instigated prior to and/or during surgery where the patient is at risk of ventricular fibrillation due to a history of myocardial infarction or other heart condition. In particular, patients who are undergoing open heart surgery (e.g. coronary by-pass grafts) may be at particular risk of imminent ventricular fibrillation. Patients whose hearts have been arrested by cooling and high potassium are at particular risk of ventricular fibrillation during rewarming of the heart and attempts to initiate normal heart beats.

In a preferred embodiment, a patient presenting with acute myocardial infarction who must receive immediate treatment to relieve the arterial occlusion by, e.g., balloon angioplasty, or otherwise remove the thrombus, may be treated with an intravenous infusion of the EPA and/or DHA emulsion prior to and during surgery.

By "calcium channel blocking omega 3 fatty acid" is meant an omega 3 fatty acid capable of inhibiting the accumulation of high concentrations of cytosolic free calcium in cardiac myoctes. Protocols for identifying omega 3 fatty acids having calcium channel blocking effects are described in Hallaq et al. (1992 *Proc Natl Acad Sci USA* 89:1760–1764).

By "EPA-DHA emulsion" is meant a suspension which comprises EPA, DHA or a mixture of both EPA and DHA. This composition is suitable for intravenous or intracardial injection into a patient.

By "injection" is meant administration of a solution, normally with a syringe and needle, directly into a selected site where the total volume of the solution is administered over a relatively short period of time (e.g. less than 5 to 10 minutes).

By "intracardial injection" is meant injection of a solution directly into the heart or an artery of the heart.

By "intravenous infusion" is meant gradual introduction of a solution directly into a vein, usually the cephalic or median basilic vein of the arm over an extended period of time (e.g. 30 minutes to several hours or days).

By "ventricular fibrillation" is meant rapid, tremulous and ineffectual contractions of the ventricles. Ventricular fibrillation may result from mechanical injury to the heart, occlusion of coronary vessels, effects of certain drugs (such as excess of digitalis, cocaine or chloroform), anaphylactic reactions or electrical stimuli.

Ventricular fibrillation may be described as two types. Primary ventricular fibrillation occurs suddenly and unexpectedly in patients with otherwise stable cardiac function. This type of fibrillation is common in the early phase of acute myocardial infarction. Resuscitation of such individuals is highly successful if treated promptly. Secondary ventricular fibrillation occurs as the terminal event in a severely failing heart. At present, resuscitation of patients with secondary ventricular fibrillation is seldom successful.

By "imminent" ventricular fibrillation is meant an emergency situation in which the patient may proceed from a medical condition involving the heart, e.g., heart attack symptoms, to subsequent ventricular fibrillation and cardiac arrest at any moment.

By "ischemia" is meant local and temporary reduction of blood flow due to obstruction of the circulation. By "myocardial ischemia" is meant local and temporary reduction of blood flow due to obstruction of the circulation to the heart.

By "ischemia-induced ventricular fibrillation" is meant ventricular fibrillation which results due to local and temporary obstruction of circulation to the heart.

By "myocardial infarction" is meant the blockage of blood flow to the heart muscle or some portion of the heart muscle that results from a relative or absolute insufficiency of blood supply.

By "patient susceptible to ventricular fibrillation" is meant an individual who presents with the conditions described above which may lead to myocardial ischemia.

DETAILED DESCRIPTION

Figure 1:
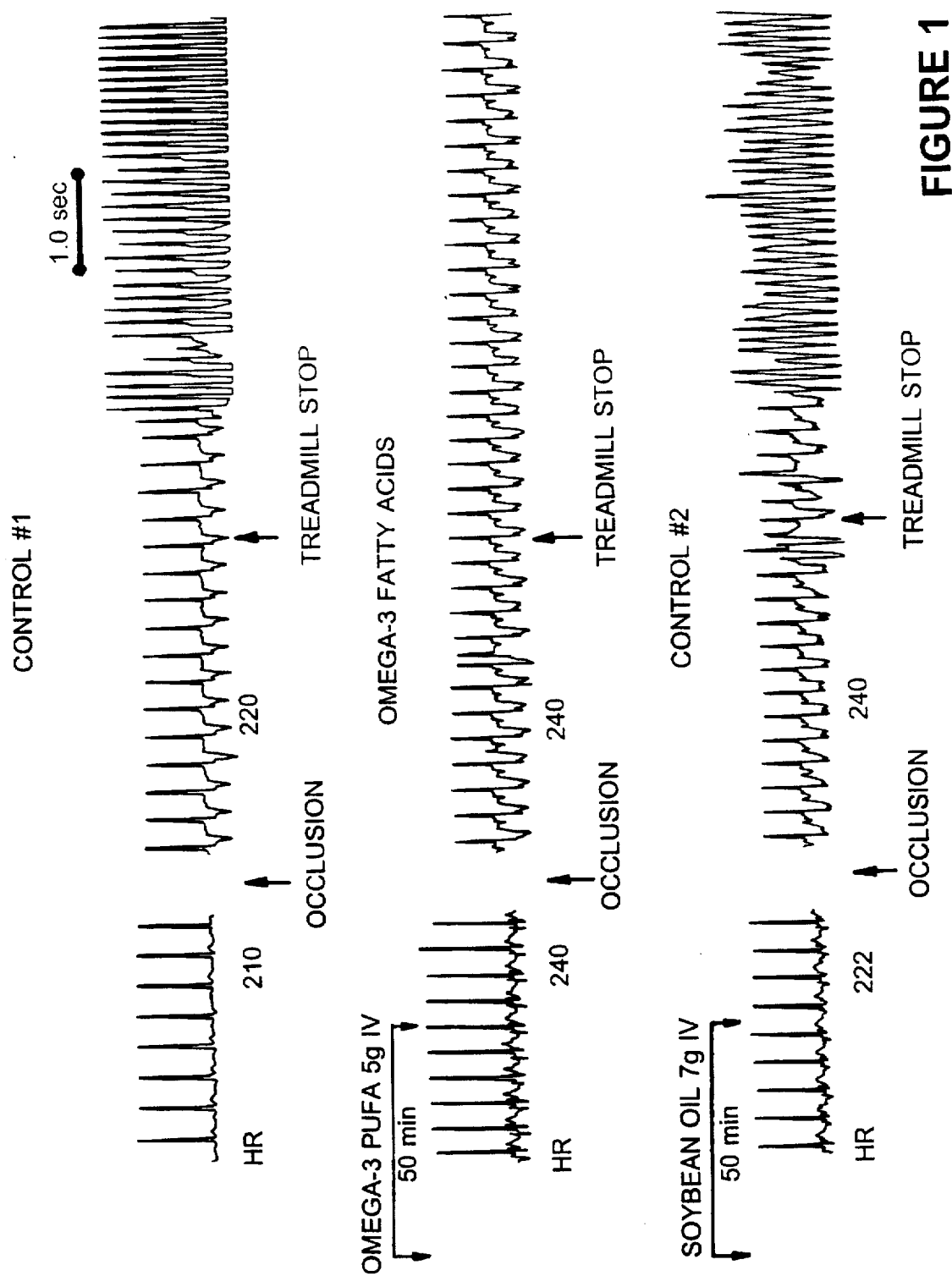

The drawing is first described.

DRAWING

The FIGURE shows representative ventricular electrograms from the same animal with and without treatment with intravenous EPA-DHA. CONTROL #1: exercise-plus-ischemia test without intravenous infusion. CONTROL #2: exercise-plus-ischemia test following a 50–60 minute infusion of a test lipid emulsion derived from soybean oil (Intralipid$^R$) which is free of EPA and DHA. OMEGA 3 FATTY ACIDS: exercise-plus-ischemia test following a 50–60 minute infusion with an EPA-DHA emulsion. Dark bar=1.0 sec, paper speed =25 mm/sec, HR=heart rate, beats/min.

INTRAVENOUS INFUSION OF EPA AND DHA PREVENTS ISCHEMIA-INDUCED VENTRICULAR FIBRILLATION

The ability of an intravenous infusion of EPA and DHA to prevent imminent primary ventricular fibrillation was demonstrated in a canine model. Mongrel dogs (14.5 to 18.3 kg) were anesthetized and instrumented to measure left circumflex coronary artery blood flow and ventricular electrogram, as previously described (Billman 1989 *J. Pharm. Expt. Therap.* 248:1334–1342; Billman et al. 1991 *FASEB J* 5:2586–2592; Billman 1992 *Eur J Pharmacol* 229:179–187; Billman 1992 *Eur J Pharmacol* 212:231–235). A hydraulic occluder was also placed around the left circumflex coronary artery and the left anterior coronary artery was ligated, producing an anterior wall myocardial infarction. The principles governing the care and treatment of animals according to the American Physiological Society were followed at all times during the experiments. In addition, the procedures used in this study were approved by the Ohio State University Institutional Animal Care and Use Committee.

The animals were walked on a motor-driven treadmill and adapted to the laboratory for a period of approximately 3 to 4 weeks after the production of the myocardial infarction. The susceptibility to ventricular fibrillation was tested in an exercise-plus-ischemia test, as previously described (Billman 1989 *J Pharm Expt Therapeutics* 248:1334–1342; Billman et al. 1991 *FASEB J* 5:2586–2592; Billman 1992 *Eur J Pharmacol* 229:179–187; Billman 1992 *Eur J Pharmacol* 212:231–235). Briefly, the animals ran on a motor-driven treadmill while work load increased every 3 minutes for 18 minutes or until a criterion heart rate of 210 beats/min (70% of maximum) was attained. During the last minute of exercise, the left circumflex coronary artery was occluded, the treadmill was stopped, and the occlusion was maintained for an additional minute to bring the total occlusion time to two minutes. Large metal plates (11 cm in diameter) were placed across the animal's chest so that electrical defibrillation could be achieved with a minimal delay, but only after the animal was unconscious. The occlusion was immediately released if malignant arrhythmias occurred.

Seven animals that developed ventricular fibrillation during this exercise-plus-ischemia test were selected for additional studies. A long experience with this canine preparation has shown that once an animal responds with ventricular fibrillation to this exercise-plus-ischemia test, that dog will always respond similarly with ventricular fibrillation (Billman 1989 *J Pharm Expt Therapeutics* 248:1334–1342). Ventricular fibrillation was induced in one additional animal by the combination of cocaine (1.0 mg/kg i.v.) and the exercise-plus-ischemia test (Billman 1993 *J Pharm Exp Therap* 266:407–416; Billman et al. 1991 FASEB J 5:2586–2592).

One week after the exercise-plus-ischemia test to identify susceptible dogs, the test was repeated after the following treatment. An emulsion of EPA and DHA in water was prepared in the following proportions: 10 ml of fish oil concentrates (EPAX 6000 FA, Pronova-Biocare, Lysaker, Norway) which contains approximately 0.7 g/ml total of EPA and DHA, with 1.5 g purified egg lecithin, 200 IU α-tocopherol, 50 mg butylated hydroxytoluene (BHT) added to 100 ml of water containing 1.25 g of glycerol with pH adjusted with sodium hydroxide to 7.4. The fish oil concentrate contained 55% by weight EPA and DHA as determined by gas chromatographic analysis. The mixture was sonicated to yield a milky white and stable emulsion. A loading dose of 15–20 ml of the emulsion was injected as a bolus over 5 minutes. This was followed by an intravenous infusion of the remainder of the emulsion over the following 50 to 60 minutes. The exercise-plus-ischemia test was then repeated as above.

One week after the test with the EPA/DHA treatment, the exercise-plus-ischemia test was repeated after treatment of the animals with either saline (n=3) or an intravenous infusion over 50–60 min of with 100 ml of Intralipid$^R$. Intralipid$^R$ (Clinitec Nutrition Co., Deerfield, Ill. 60015) is a 10% lipid emulsion (n=5) containing soy bean oil with only some 7% by weight (as determined by gas chromatography) of another omega 3 fatty acid, α-linolenic acid (18:3n-3) (Reeves and Weihrauch Composition of Foods, Agriculture Handbook No. 8-4, Washington, D.C.: U.S. Department of Agriculture, 1979), but no EPA or DHA.

In all experiments, cardiac function was monitored by ventricular electrocardiography and an intraventricular transducer for left ventricular pressure (n=3). A pulsed Doppler flow transducer around the left circumflex coronary artery was used to confirm completeness of the coronary artery occlusion. Heart rate was averaged over the last 5 sec of each exercise level, immediately before and at the end of the 60 sec (or immediately before ventricular fibrillation) time points during the occlusion.

The initial 4 dogs studied were infused with 10 ml of an EPA-DHA emulsion which was prepared from a fish oil concentrate containing 70% total omega 3 fatty acids with free EPA and DHA comprising 33.9 and 25.0% by weight of that total, respectively, as determined by gas chromatography. A further 4 animals received an emulsion containing 5.0 ml of the same free fatty acid preparation and 5.0 ml of triglyceride concentrate containing 65% by weight total omega 3 fatty acids with EPA and DHA composing 34.0% and 23.6% by weight of that total, respectively as determined by gas chromatography.

The data were analyzed using a two factor (drug x occlusion) analysis of variance (ANOVA) for repeated measures. When the F-ratio was found to exceed a critical value ($p<0.05$), Scheffe's test was used to compare the means. The effect of the omega 3 fatty acids on ventricular fibrillation were determined using a Chi-square test with Yate's correction for continuity. All data are reported as the mean ± SEM. Cardiac arrhythmias were analyzed at a paper speed of 25 mm/sec.

Representative ventricular electrogram recordings obtained from the same animal before and after pretreatment with the EPA-DHA emulsion are displayed in the FIGURE. Ventricular flutter (which degenerates to ventricular fibrillation) was reproducibly induced in the control animals that received either no infusion (Control #1) or a control infusion of saline or Intralipid$^R$ (Control #2) during the exercise-plus-ischemia tests. The dog treated with cocaine and subjected to the exercise-plus-ischemia test responded similarly. The average time to the onset of ventricular fibrillation was 55.1±2.8 sec (range from 42 to 63.4 sec); 4 animals developed ventricular fibrillation shortly after the treadmill stopped, whereas 4 developed malignant arrhythmias while running. In contrast, EPA-DHA infusion prevented ventricular arrhythmias in 7 (including the cocaine-induced ventricular fibrillation) of the 8 (87.5%) susceptible animals (Chi-square=9.14, p<0.005).

The EPA-DHA infusion evoked significant reductions in heart rate (drug effect F=7.86, p<0.05) both before (control, 211.4±16.5 versus EPA-DHA 163.6±17.0 beats/min) and during the coronary occlusion (control 227.4±16.1 versus EPA-DHA 164.9±22.8 beats/min). The intravenous infusion of EPA-DHA reduced heart rate in 6 of the 8 animals, while increasing heart rate in two animals. Both animals with the increased heart rate were still protected by the infusions of the EPA-DHA emulsion. In a similar manner, P-R intervals significantly (p<0.01) increased after the infusion of EPA-DHA (control 91.7±5.5 versus EPA-DHA 108.9±6.8 msec); second degree (2:1) atrioventricular (AV) block was, in fact, induced in 4 of the 8 animals.

Preparation/Isolation of EPA and DHA

EPA and DHA, as well as ethyl esters and methyl esters of EPA and DHA, may be obtained from commercial sources (e.g., Sigma). EPA and DHA may also be isolated from fish oil employing methods known in the art (Yamazaki et al. 1991 *Am J Clin Nutr* 53:620–627). Alternative methods of preparation are known in the art. Rather than administering isolated EPA and/or DHA, a fish oil concentrate may also be employed.

Other omega 3 fatty acids of interest which may be found in fish oil concentrates include those fatty acids having calcium channel blocking activity. Methods for the identification, isolation and screening of these fatty acids is known in the art (Hallaq et al. 1992 *Proc. Natl. Acad. Sci. USA* 89:1760–1764).

Preparation of EPA-DHA for Administration

EPA and/or DHA may be administered as a suspension in a physiologically acceptable carrier suitable for intravenous injection into a patient, e.g. sterile saline. Salts (e.g. sodium salts) of EPA and/or DHA rather than the free fatty acid, may be employed. To facilitate suspension, (i.e. formation of an emulsion), a suitable emulsifying agent (e.g., lecithin) may be used. The EPA-DHA emulsion may further include additional agents such as anti-thrombotic agents, blood thinning agents, pain-relieving agents, and nutrients such as glucose.

Identification of Patients

The therapy of the invention can be employed for acute treatment of a patient presenting with a myocardial infarction or other condition which renders the patient susceptible to imminent ventricular fibrillation which may result in sudden death.

Myocardial infarction is usually associated with a classic clinical syndrome with sudden onset of characteristic symptoms, followed by serial electrocardiographic changes and transient rises in the serum levels of enzymes released from the myocardium. In the classic syndrome, a sudden, total occlusion of a major coronary artery by thrombosis causes infarction involving virtually the full thickness of the left ventricular wall in the specific region supplied by the affected artery. In these cases, the artery is usually totally occluded within six hours after the onset of symptoms. In other instances the occlusion of the artery is less sudden or less complete and the resulting infarction occurs during a period of hours or days and may be less localized.

Myocardial infarction may result in deaths that occur instantaneously or within minutes after the onset of ischemic symptoms. Myocardial infarction may arise from a sudden severe disparity between myocardial oxygen supply and demand in the absence of acute changes in the caliber of the coronary arteries; for example, a sudden reduction in oxygen supply caused by a drop in blood pressure during anesthesia and surgery may precipitate myocardial infarction. An acute increase in oxygen demand resulting from such stresses as heavy exertion, acute hypertension, an excess of catecholamines or cocaine abuse may also precipitate myocardial infarction. Myocardial fibrosis, which results from ischemia to heart muscle, may also predispose an individual to ventricular fibrillation when subjected to a further acute ischemic event. The initial myocardial fibrosis may develop during a period of months or years in patients with coronary artery disease who do not present with acute clinical episodes.

In patients presenting with classical acute myocardial infarction, the first symptom is usually chest pain, typically similar to angina pectoris but more severe, more persistent, and unrelieved by nitroglycerin. Radiation of the pain or its localization to the neck, jaw, shoulder or left arm occurs as in angina; pain in the epigastrium, simulating that of indigestion, is particularly frequent. Marked sweating, almost from the onset of pain, is characteristic, and nausea and vomiting are common.

Physical examination typically reveals a patient with continuing chest pain who prefers to lie quietly in the supine position and is in evident acute distress. The skin is usually cool, moist and pale. The pulse may be rapid or slow and the blood pressure may be elevated or reduced. Heart sounds are often faint and an $S_4$ (atrial gallop) is often present. An $S_3$ (ventricular gallop), inspiratory rales and elevated jugular venous pressure are signs of congestive heart failure and are observed in only a minority of patients at the initial presentation. Pericardial friction rubs are rarely heard initially. Electrocardiogram (ECG) examination reveals the development of pathological Q waves and serial ST segment and T wave changes. These patterns are virtually diagnostic in themselves. Some patients may present with only changes in the ST segments and T waves. Two-dimensional echocardiography demonstrates abnormalities that occur in acute myocardial infarction as early as the within the first few minutes or hours after onset. This procedure is useful in the initial evaluation of the patient, particularly when the ECG is not diagnostic or the diagnosis is in doubt. The extent of the wall motion abnormality is helpful in assessment of the initial prognosis and likelihood of complications. Abnormal bulging of the atrial septum toward the left atrium in patients with acute inferior myocardial infarction is an indicator of right ventricular infarction.

Not all patients with acute myocardial infarction present with classical symptoms. For example, diabetic patients may be especially likely to have acute myocardial infarction without experiencing chest pain because of neuropathy involving the neural pathways in the thorax that carry visceral pain signals. (Airaksinen et al. 1992 association between silent coronary artery disease, diabetes and autonomic neuropathy: fact or fallacy? *Diabetes Care* 15:288). Onset of myocardial infarction in elderly patients presents most frequently presents with sudden dyspnea or exacerbation of chronic congestive heart failure. Acute confusion, dizziness, syncope, stroke or new arrhythmia may also be the presenting symptom. (Aronow 1987 Prevalence of presenting symptoms of recognized acute myocardial infarction and of unrecognized healed myocardial infarction in elderly patients. *Am J Cardiol* 60:1182) Postoperative infarction may be difficult to recognize by classical symptoms due to concurrent medical circumstances (e.g. pain, use of analgesic drugs).

Laboratory diagnosis during acute phase reveals a rise in serum levels of creatine kinase or its MB isoenzyme, which is detectable within 3 hours after pain onset in typical cases of acute myocardial infarction. Levels of lactate dehydrogenase (LDH) are also indicative of the onset of acute myocardial infarction; LDH levels remain elevated for up to a week or longer after onset. Radionuclide imaging or magnetic resonance imaging may also be employed in diagnosis of infarction.

Patients who have had a previous infarction experience a recurrence of myocardial infarction after noncardiac surgery, particularly after thoracic or abdominal surgery or when surgery is performed within 6 months after an infarction. (Steen et al. 1978 Myocardial reinfarction after anesthesia and surgery *JAMA* 239:2566) Incidence of mortality in such cases is high.

Timing of Administration

The EPA-DHA emulsion may be administered to the patient immediately upon presentation of symptoms associated with risk of imminent ventricular fibrillation, such as those associated with acute myocardial infarction. Treatment may be continued until the arterial occlusion is relieved (e.g. balloon angioplasty) and/or the patient is in stable or noncritical condition. Treatment may be continued for up to one week, usually no longer than 4 days, more usually no longer than 48 hours.

Mode of Administration

Where the patient presents with symptoms which constitute an emergency situation (e.g. symptoms of heart attack and imminent ventricular fibrillation), the patient may receive an initial bolus of the EPA-DHA emulsion by direct injection into the heart or an artery of the heart. As an alternative or supplement to the direct intracardial injection, the patient may receive the EPA-DHA emulsion as an intravenous infusion. The EPA-DHA emulsion may be administered from a container adapted for the desired mode of administration, such as an I.V. bottle for intravenous infusion or from a syringe and needle for direct intracardial injection.

Dosages of the EPA-DHA emulsion appropriate for human use can be extrapolated from dosages appropriate for non-human animal use depending on the weight of the animal. For example, it is expected that the concentrations of EPA and/or DHA and the rate of delivery found to be appropriate for dogs will be comparable to the parameters appropriate for human admnistration. In dogs, a total dosage of as little as about 2 g and up to about 5 g of EPA and DHA was found to be effective in the prevention of imminent ventricular fibrillation.

While the concentrations of each of DHA and EPA in the emulsion may vary, the total concentration of EPA and DHA should be less than 10 to 30% by volume of the emulsion where EPA and/or DHA are not conjugated to a carrier and the emulsion is administered at normal intravenous infusion rates which are well known in the art. Appropriate, physiologically acceptable carriers for use in the EPA-DHA emulsion are known in the art. Emulsions with concentrations greater than 10 to 30% by volume EPA-DHA are not desirable for direct intravenous infusion due to the toxicity associated with administration of high concentrations of EPA and/or DHA.

Encapsulation of EPA and/or DHA in lipid vesicle carriers can allow for non-toxic administration of emulsions comprising greater than 10 to 30% by volume EPA and/or DHA. Lipid vesicles made of, for example, egg lecithin may allow for slow release of the EPA and/or DHA. Alternatively, although less desirably, the toxicity of administration of emulsions comprising total concentrations of EPA and/or DHA greater than 10 to 30% by volume may be avoided by reducing the rate of intravenous infusion.

The emulsion may comprise EPA, DHA or a mixture or EPA and DHA at a concentration usually at least 5% to 10% by volume, with a final total dosage of 3.5 g to 7 g EPA and/or DHA being administered to the patient. A final total dosage of 2 g of EPA and/or DHA or less may be effective. The total amount of EPA and/or DHA may be administered as an intrvenous infusion at a rates ranging from approximately $5 \times 10^{-7}$ to $2 \times 10^{-5}$ mole/kg/min.

What is claimed is:

1. A method for preventing imminent ventricular fibrillation, said method comprising the steps of:

identifying a patient at risk of imminent ventricular fibrillation; and infusing intravenously into said patient a composition comprising eicosapentaenoic acid, in an amount being sufficient to prevent imminent ventricular fibrillation.

2. The method of claim 1, wherein said patient at risk of imminent ventricular fibrillation has had a myocardial infarction.

3. The method of claim 1, wherein said infusing is carried out within three hours of the onset of myocardial infarction.

4. The method of claim 1, wherein said composition comprises at least 5% by volume eicosapentaenoic acid.

5. The method of claim 1, further comprising, prior to the step of infusing said composition, the step of injecting said composition intracardially into said patient.

6. The method of claim 5, wherein said patient at risk of imminent ventricular fibrillation has had a myocardial infarction.

7. The method of claim 5, wherein said composition comprises at least 5% by volume eicosapentaenoic acid.

8. The method of claim 1, wherein said patient is at risk of imminent secondary ventricular fibrillation.

9. The method of claim 1, wherein said eicosapentaneoic acid is in the form of a free acid.

10. The method of claim 1, wherein said eicosapentaneoic acid is in the form of a salt.

11. A method for preventing imminent ventricular fibrillation, said method comprising the steps of:

identifying a patient at risk of imminent ventricular fibrillation; and injecting intracardially into said patient a composition comprising eicosapentaenoic acid, in an amount being sufficient to prevent imminent ventricular fibrillation.

12. The method of claim 11, wherein said patient at risk of imminent ventricular fibrillation has had a myocardial infarction.

13. The method of claim 11, wherein said injecting is carried out within three hours of the onset of myocardial infarction.

14. The method of claim 11, wherein said patient is at risk of imminent secondary ventricular fibrillation.

15. The method of claim 11, wherein said eicosapentaneoic acid is in the form of a free acid.

16. The method of claim 11, wherein said eicosapentaneoic acid is in the form of a salt.

* * * * *